United States Patent
Kim et al.

(10) Patent No.: US 12,011,443 B2
(45) Date of Patent: Jun. 18, 2024

(54) PHARMACEUTICAL COMPOSITION FOR PREVENTING OR TREATING NONALCOHOLIC STEATOHEPATITIS

(71) Applicant: J2H BIOTECH INC., Suwon-Si (KR)

(72) Inventors: Jae-Sun Kim, Suwon-si (KR);
Hyung-Chul Ryu, Osan-Si (KR);
Jee-Woong Lim, Seongnam-Si (KR);
Jung-Gun Joung, Hwaseong-Si (KR);
Sun-Joo Kim, Suwon-Si (KR);
Yeon-Woo Son, Hwaseong-Si (KR);
Hyung-Jun Kim, Asan-Si (KR);
Wenling Song, Uiwang-Si (KR)

(73) Assignee: J2H BIOTECH INC., Suwon-si (KR)

( * ) Notice: Subject to any disclaimer, the term of this patent is extended or adjusted under 35 U.S.C. 154(b) by 794 days.

(21) Appl. No.: 17/262,084

(22) PCT Filed: Jul. 19, 2019

(86) PCT No.: PCT/KR2019/008963
§ 371 (c)(1),
(2) Date: Jan. 21, 2021

(87) PCT Pub. No.: WO2020/022708
PCT Pub. Date: Jan. 30, 2020

(65) Prior Publication Data
US 2021/0299127 A1    Sep. 30, 2021

(30) Foreign Application Priority Data

Jul. 23, 2018 (KR) ........................ 10-2018-0085431

(51) Int. Cl.
*A61K 31/506* (2006.01)
*A61P 1/16* (2006.01)

(52) U.S. Cl.
CPC .............. *A61K 31/506* (2013.01); *A61P 1/16* (2018.01)

(58) Field of Classification Search
CPC .................................................. A61K 31/506
See application file for complete search history.

(56) References Cited

U.S. PATENT DOCUMENTS

| | | | |
|---|---|---|---|
| 2011/0009391 A1 | 1/2011 | Braun et al. | |
| 2012/0135958 A1 | 5/2012 | Namane et al. | |
| 2015/0056223 A1 | 2/2015 | Lim et al. | |
| 2018/0140509 A1 | 5/2018 | Grogan, Jr. | |
| 2018/0140609 A1 | 5/2018 | Lamothe et al. | |

FOREIGN PATENT DOCUMENTS

| | | |
|---|---|---|
| CN | 107530355 A | 1/2018 |
| JP | 2004528308 A | 9/2004 |
| KR | 20110123657 A | 11/2011 |
| RU | 2635966 C2 | 11/2017 |
| WO | 02076435 A2 | 10/2002 |
| WO | 2011/139107 A2 | 11/2011 |

OTHER PUBLICATIONS

International Search Report dated Oct. 24, 2019 for International Patent Application No. PCT/KR2019/008963, 20 pages with English translation.
Oh et al., "A potent and selective 11β-hydroxysteroid dehydrogenase type 1 inhibitor, SKI2852, ameliorates metabolic syndrome in diabetic mice models", European Journal of Pharmacology, 2015, vol. 768, pp. 139-148.
Zou et al., "11Beta-Hydroxysteroid Dehydrogenase-1 Deficiency or Inhibition Enhances Hepatic Myofibroblast Activation in Murine Liver Fibrosis", 2018, vol. 67, No. 6, pp. 2167-2181.
Dowman et al., "Pathogenesis of non-alcoholic fatty liver disease", Q J Med, 2010, vol. 103, pp. 71-83.
Jae Sung Ko, "Nonalcoholic Fatty Liver Disease", Korean J Gastroenterol, 2010, vol. 56, pp. 6-14 with English abstract.
Stefan et al., "Inhibition of 11β-HSD1 with RO5093151 for non-alcoholic fatty liver disease: a multicentre, randomised, double-blind, placebo-controlled trial", Lancet Diabetes Endocrinol, 2014, vol. 2, pp. 406-416.
Woods et al., "Glucocorticoids and Non-Alcoholic Fatty Liver Disease", The Journal of Steroid Biochemistry & Molecular Biology, dx.doi.org/10.1016/j.jsbmb.2015.07.020, pp. 1-33.
Chen et al., "Gossypol ameliorates liver fibrosis in diabetic rats induced by high-fat diet and streptozocin", Life Sciences, 2016, vol. 149, pp. 58-64.
Ryu et al., "Discovery of 2-((R)-4-(2-Fluoro-4-(methylsulfonyl)phenyl)-2-methylpiperazin-1-yl)-N-((1R,2s,3S,5S,7S)-5-hydroxyadamantan-2-yl)pyrimidine-4-carboxamide (SKI2852): A Highly Potent, Selective, and Orally Bioavailable Inhibitor of 11β-Hydroxysteroid Dehydrogenase Type 1 (11β-HSD1)", Journal of Medicinal Chemistry, 2016, vol. 59, pp. 10176-10189.
Larner et al., "Male 11β-HSD1 Knockout Mice Fed Trans-Fats and Fructose are Not Protected From Metabolic Syndrome or Nonalcoholic Fatty Liver Disease", Endocrinology, Sep. 2016, vol. 157, No. 9, pp. 3493-3504.

*Primary Examiner* — Rebecca L Anderson
(74) *Attorney, Agent, or Firm* — MH2 TECHNOLOGY LAW GROUP, LLP

(57) ABSTRACT

The present invention relates to a medical use of a compound, of Chemical Formula 1, for treating, alleviating or preventing non-alcoholic steatohepatitis (NASH) and/or hepatic fibrosis.

3 Claims, 3 Drawing Sheets

【Figure 1】
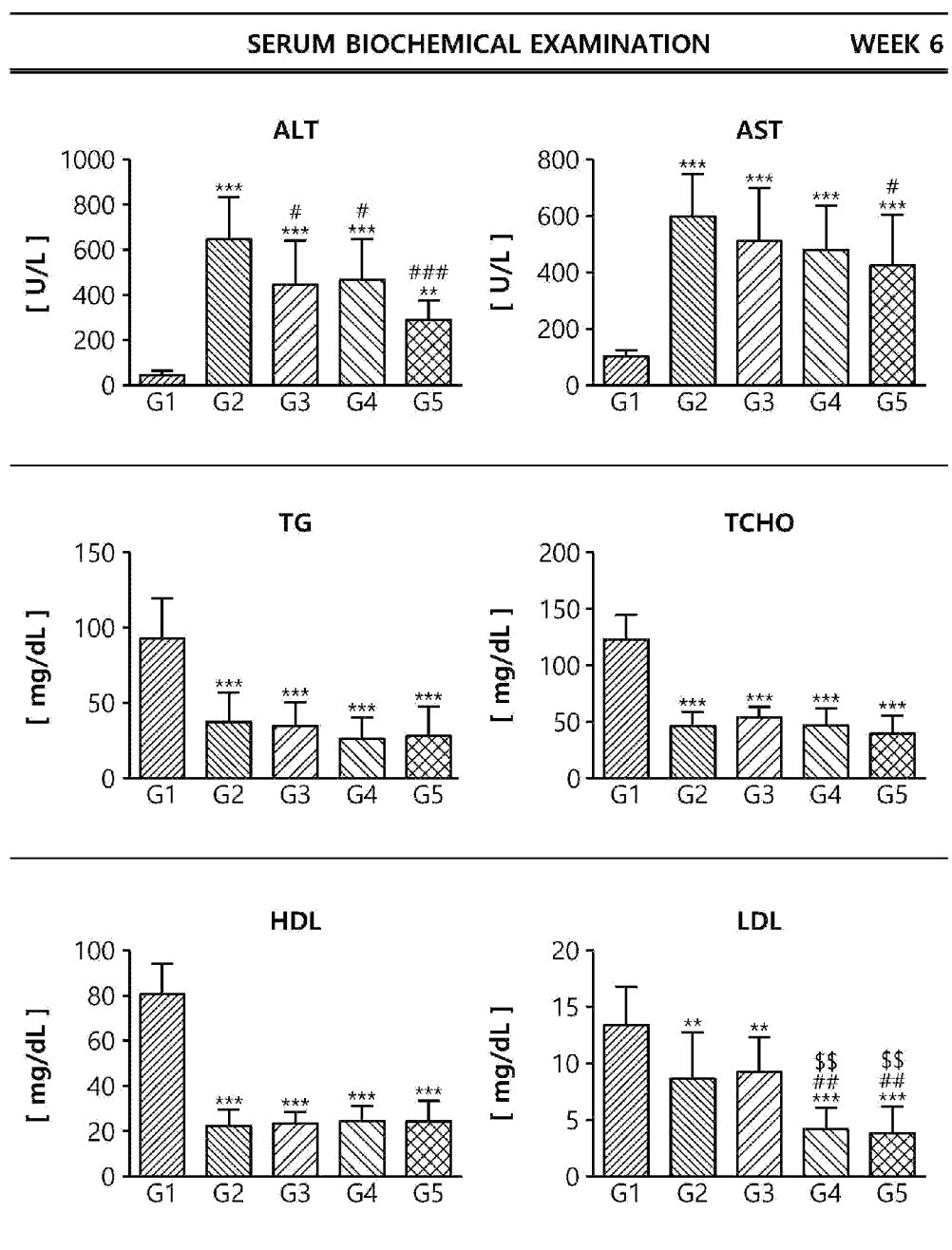

[Figure 2]
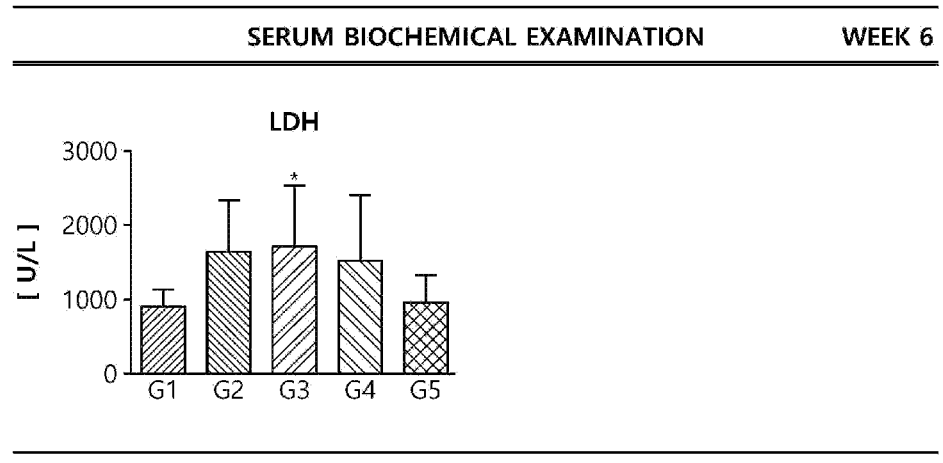
[Figure 3]
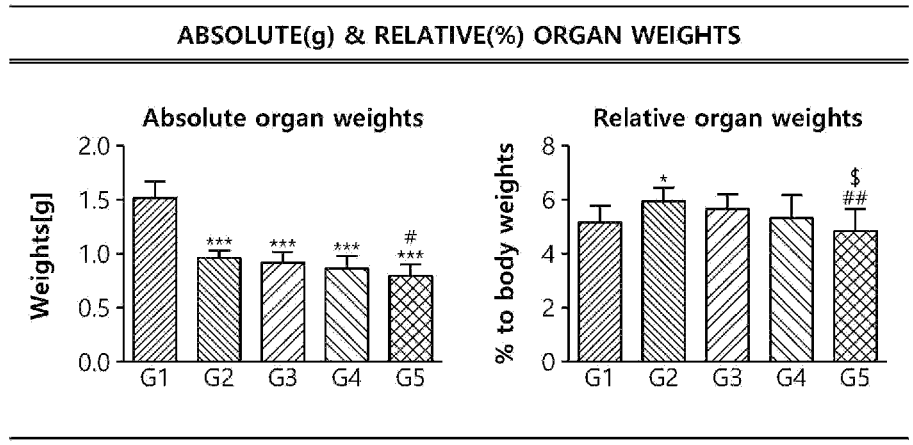
[Figure 4]
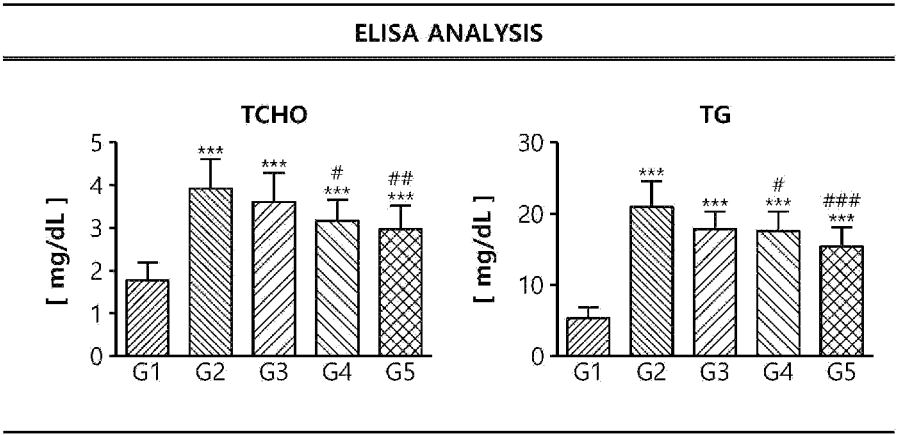

【Figure 5】
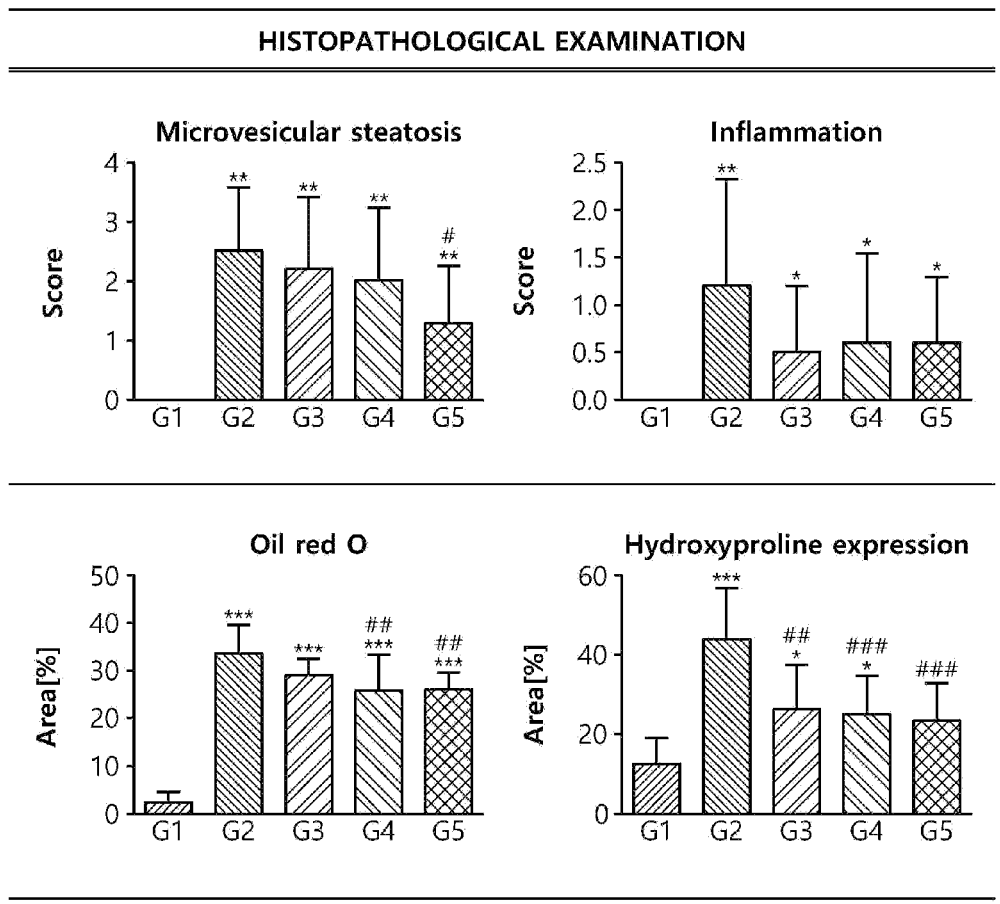
【Figure 6】
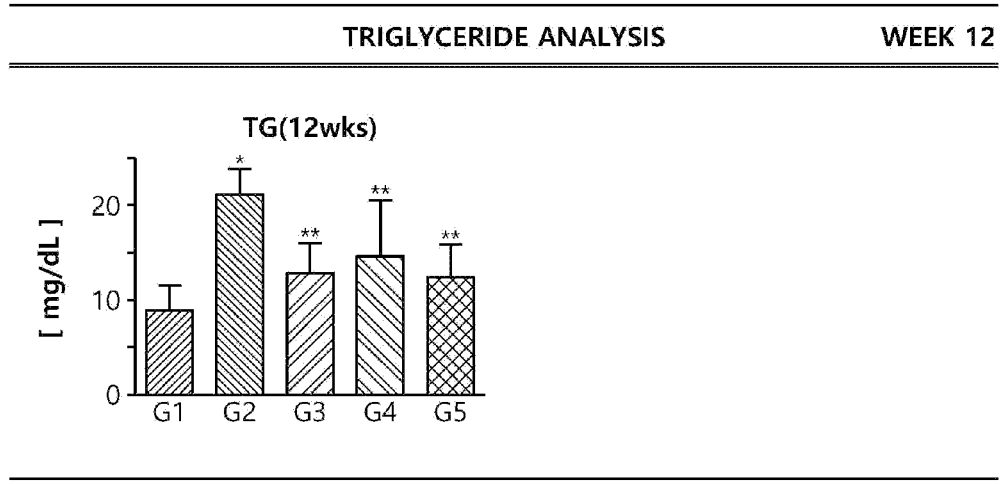

PHARMACEUTICAL COMPOSITION FOR PREVENTING OR TREATING NONALCOHOLIC STEATOHEPATITIS

CROSS-REFERENCE TO RELATED APPLICATIONS

This application is a U.S. National Stage application of PCT/KR2019/008963 filed 19 Jul. 2019, which claims priority to Korean Patent Application No. 10-2018-0085431 filed 23 Jul. 2018.

TECHNICAL FIELD

The present disclosure relates to a pharmaceutical composition for treating or preventing non-alcoholic steatohepatitis. The present disclosure also relates to a pharmaceutical composition for treating or preventing liver fibrosis.

BACKGROUND ART

The worldwide prevalence of non-alcoholic steatohepatitis reaches 2 to 4% (US 3 to 5%). Unlike simple steatohepatitis, such non-alcoholic steatohepatitis shows pathological findings such as ballooning degeneration, cell death, and inflammatory infiltration, and in some cases, fibrosis such as collagen accumulation may be shown. It is well known that simple steatosis shows slow histological progression, whereas non-alcoholic steatohepatitis shows a faster histological progression and can progress to cirrhosis. About 5 to 10% of people found to have fatty liver prove to also have steatohepatitis (Metabolism Clinical and Experimental 65 (2016) 1038-1048).

Currently, there is no commercially available treatment to treat such steatohepatitis, and due to the absence of treatment, other metabolic syndrome treatments such as abdominal obesity, hyperlipidemia, diabetes, for example, insulin resistance improvement drugs, antioxidants (for example, vitamins C, E), dyslipidemia drugs, hepatoprotective drugs, etc. are used, but these are not considered direct treatments for non-alcoholic steatohepatitis.

Meanwhile, 2-((R)-4-(2-fluoro-4-(methylsulfonyl)phenyl)-2-methylpiperazin-1-yl)-N-((1R,2s,3S,5S,7S)-5-hydroxyadamantan-2-yl)pyrimidine-4-carboxamide represented by the following Chemical Formula 1 (hereinafter, abbreviated as 'pyrimidine-4-carboxamide') is a compound included in the formula disclosed in PCT Publication No. WO2011-139107.

[Chemical Formula 1]

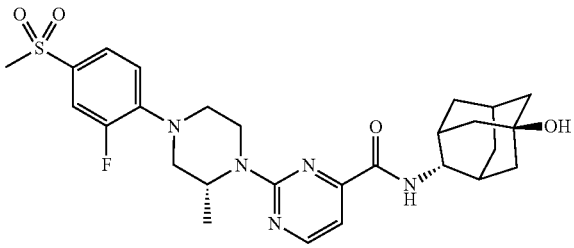

The compound of the Chemical Formula 1 is an inhibitor of 11β-Hydroxysteroid Dehydrogenase Type 1 (11β-HSD1), which has been developed as a therapeutic agent for type 2 diabetes. However, as with other 11β-HSD1 inhibitors, its development was discontinued because a single administration and combined administration with metformin (diabetes medication), did not show sufficient efficacy.

DISCLOSURE

Technical Problem

Therefore, the problem to be solved by the present invention is to provide a pharmaceutical composition useful for treatment, alleviation or prevention of non-alcoholic steatohepatitis.

Furthermore, the problem to be solved by the present invention is to provide a pharmaceutical composition useful for treatment, alleviation or prevention of liver fibrosis.

Technical Solution

In order to solve the above problems, the present disclosure provides a pharmaceutical composition for treating, alleviating, or preventing non-alcoholic steatohepatitis, comprising a pyrimidine-4-carboxamide compound of Chemical Formula 1 as an active ingredient.

[Chemical Formula 1]

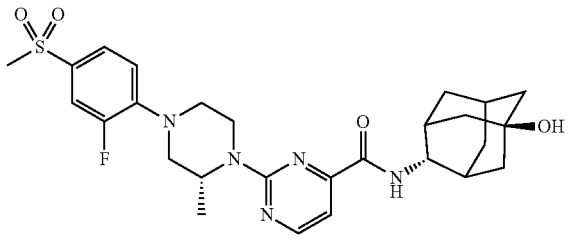

The present disclosure also provides a pharmaceutical composition for alleviating, preventing, or treating non-alcoholic steatohepatitis accompanied by liver fibrosis, comprising the compound of Chemical Formula 1 as an active ingredient.

The present disclosure also provides a pharmaceutical composition for alleviating, preventing or treating liver fibrosis comprising the compound of Chemical Formula 1 as an active ingredient.

The present disclosure also provides a method for alleviating, treating or preventing non-alcoholic steatohepatitis (preferably accompanied by liver fibrosis) and/or liver fibrosis comprising administering to a subject in need of treatment, alleviation or prevention of non-alcoholic steatohepatitis and/or liver fibrosis a therapeutically or prophylactically effective amount of the compound of Chemical Formula 1.

That is, the present disclosure provides a medical use of the compound of Chemical Formula 1 for the treatment, alleviation or prevention of non-alcoholic steatohepatitis (preferably non-alcoholic steatohepatitis accompanied by liver fibrosis) and/or liver fibrosis.

The present inventors completed this invention by confirming that the concentration of the liver tissue was higher than the plasma concentration when measuring the tissue concentration of the compound of Chemical Formula 1, 2 hours after oral administration to the mouse, and then also confirming the efficacy after the oral administration in the non-alcoholic steatohepatitis animal model (prevention and treatment).

The compound of Chemical Formula 1 of the present invention reduces the lipid content of the liver tissue, has the effect of treating inflammation of the liver tissue, and has the effect of inhibiting fibrosis of the liver tissue, thus can be usefully used for alleviating, preventing and treating non-alcoholic steatohepatitis.

As used herein, the term "prevention" includes the prevention of the recurrence, spread or onset of non-alcoholic steatohepatitis or liver fibrosis in a patient.

As used herein, the term "treatment" includes the eradication, removal, modification, or control of non-alcoholic steatohepatitis or liver fibrosis; and minimizing or delaying the spread of non-alcoholic steatohepatitis or liver fibrosis.

The compound of Chemical Formula 1 may be prepared by the method disclosed in PCT Publication No. WO2011-139107.

As used herein, the phrase "compound of this/the disclosure" includes the compound or pharmaceutically acceptable salt(s) of Chemical Formula 1, as well as clathrates, hydrates, solvates, or polymorphs thereof.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

If any compound (prodrug) produces the compound or its salt of this disclosure after degrading in vivo, such compound is included in this disclosure. As used herein and unless otherwise indicated, the term "prodrug" means a compound that can hydrolyze, oxidize, or otherwise react under biological conditions (in vitro or in vivo) to provide an active compound, particularly a compound of this disclosure. Examples of prodrugs include, but are not limited to, metabolites of a compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* $6^{th}$ ed. (Donald J. Abraham ed., 2001, Wiley) and *Design and Application of Prodrugs* (H. Bundgaard ed., 1985, Harwood Academic Publishers Gmfh).

The compound of the present disclosure is generally administered in a therapeutically effective amount.

The compound of the present disclosure can be administered by any suitable route in the form of a pharmaceutical composition adapted to such a route, and in a dose effective for the treatment intended. An effective dosage is typically in the range of about 0.01 to about 50 mg per kg body weight per day, preferably about 0.05 to about 20 mg/kg/day, in single or divided doses. Depending on age, species and disease or condition being treated, dosage levels below the lower limit of this range may be suitable. In other cases, still larger doses may be used without harmful side effects. Larger doses may also be divided into several smaller doses, for administration throughout the day. Methods for determining suitable doses are well known in the art to which the present disclosure pertains. For example, Remington: The Science and Practice of Pharmacy, Mack Publishing Co., 20th ed., 2000 can be used.

In another embodiment, there is provided a pharmaceutical composition comprising the compound of Chemical Formula 1 or a pharmaceutically acceptable salt thereof, and a pharmaceutically acceptable carrier or additive.

The term "pharmaceutically-acceptable" means suitable for use in pharmaceutical preparations, generally considered as safe for such use, officially approved by a regulatory agency of a national government for such use, or being listed in South Korean or the U. S. Pharmacopoeia for use in humans.

For the treatment of the diseases or conditions referred to above, the compound described herein or pharmaceutically acceptable salts thereof can be administered as follows:

Oral Administration

The compound of the present disclosure may be administered orally, including by swallowing, so that the compound enters the gastrointestinal tract, or absorbed into the blood stream directly from the mouth (e.g., buccal or sublingual administration).

Suitable compositions for oral administration include solid, liquid, gel or powder formulations, and have a dosage form such as tablet, lozenge, capsule, granule or powder.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form, the amount of the active ingredient present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, lactose, starch, sodium starch glycolate, crospovidone, croscarmellose sodium, maltodextrin, or mixtures thereof.

Suitable lubricants, for use in a tablet, may be present in amounts from about 0.1% to about 5% by weight, and include, but are not limited to, talc, silicon dioxide, stearic acid, calcium, zinc or magnesium stearate, sodium stearyl fumarate and the like.

Suitable binders, for use in a tablet, include, but are not limited to, gelatin, polyethylene glycol, sugars, gums, starch, polyvinyl pyrrolidone, hydroxypropyl cellulose, hydroxypropylmethyl cellulose and the like. Suitable diluents, for use in a tablet, include, but are not limited to, mannitol, xylitol, lactose, dextrose, sucrose, sorbitol, microcrystalline cellulose and starch.

Suitable solubilizers, for use in a tablet, may be present in amounts from about 0.1% to about 3% by weight, and include, but are not limited to, polysorbates, sodium lauryl sulfate, sodium dodecyl sulfate, propylene carbonate, diethyleneglycol monoethyl ether, dimethyl isosorbide, polyoxyethylene glycolic (natural or hydrogenated) castor oil, HCOR™ (Nikkol), oleyl ester, Gelucire™, caprylic/caprylic acid mono/diglyceride, sorbitan fatty acid esters, and Solutol HS™.

Parenteral Administration

Compounds of the present disclosure may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release.

Most parenteral formulations are aqueous solutions containing excipients, including salts, buffering agents and isotonic agents.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Topical Administration

The compound of the present disclosure may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical administration can also be performed by electroporation, iontophoresis, phonophoresis and the like.

Compositions for topical administration may be formulated as immediate or modified release, including delayed or sustained release.

References for Preparing Pharmaceutical Compositions

Methods for preparing pharmaceutical compositions for treating or preventing a disease or condition are well known in the art to which the present disclosure pertains. For example, based on *Handbook of Pharmaceutical Excipients* (7$^{th}$ ed.), Remington: *The Science and Practice of Pharmacy* (20th ed.), *Encyclopedia of Pharmaceutical Technology* (3$^{rd}$ ed.), or *Sustained and Controlled Release Drug Delivery Systems* (1978), pharmaceutically acceptable excipients, carriers, additives and so on can be selected and then mixed with the compounds of the present disclosure for making the pharmaceutical compositions.

Advantageous Effects

The present disclosure provides a pharmaceutical composition useful for alleviating, treating or preventing non-alcoholic steatohepatitis or liver fibrosis, comprising the compound of Chemical Formula 1 as an active ingredient. That is, the present disclosure provides a medical use of the compound of Chemical Formula 1, which is useful for alleviating, treating or preventing non-alcoholic steatohepatitis or liver fibrosis.

BRIEF DESCRIPTION OF DRAWINGS

In the following figures, data are presented as mean±S.D (G1: Normal control, G2: Vehicle control, G3: Positive control 10 mg/kg/day, G4: Test compound 10 mg/kg/day, G5: Test compound 30 mg/kg/day).

FIG. 1 shows the results of blood biochemical analysis after 6 weeks of administration in a non-alcoholic steatohepatitis disease model.

\*\*\*/\*\*: There is a significant difference at the level of $p<0.001/p<0.01$, respectively, compared to G1.

/##/#: There is a significant difference at the level of $p<0.001/p<0.01/p<0.05$, respectively, compared to G2.

$$: There is a significant difference at the level of $p<0.01$ compared to G3.

FIG. 2 is a result of measuring LDH (Lactate Dehydrogenase).

\*: There is a significant difference at the level of $p<0.05$ compared to G1.

FIG. 3 shows the absolute weight and relative weight of the liver, respectively.

\*\*\*/\*: There is a significant difference at the level of $p<0.001/p<0.05$, respectively, compared to G1.

/#: There is a significant difference at the level of $p<0.01/p<0.05$, respectively, compared to G2.

$: There is a significant difference at the level of $p<0.05$ compared to G3.

FIG. 4 is a result of measuring total cholesterol and triglycerides in liver tissue using ELISA. It can be seen that TCHO and TG decreased in a dose-dependent manner in the test compound administration group.

\*\*\*: There is a significant difference at the level of $p<0.05$ compared to G1.

/##/#: There is a significant difference at the level of $p<0.001/p<0.01/p<0.05$, respectively, compared to G2.

FIG. 5 is a histopathological test result.

\*\*\*/\*: There is a significant difference at the level of $p<0.001/p<0.01/p<0.05$, respectively, compared to G1.

/##/#: There is a significant difference at the level of $p<0.001/p<0.01/p<0.05$, respectively, compared to G2.

FIG. 6 is a result of analysis of triglycerides in hepatocytes in a test model for evaluating the preventive effect of the compound of the present invention.

\*: There is a significant difference at the level of $p<0.05$ compared to G1.

\*\*: There is a significant difference at the level of $p<0.05$ compared to G2.

MODE FOR INVENTION

Hereinafter, the present disclosure is described in considerable detail with examples to help those skilled in the art understand the present disclosure. However, the following examples are offered by way of illustration and are not intended to limit the scope of the invention. It is apparent that various changes may be made without departing from the spirit and scope of the invention or sacrificing all its material advantages.

Example 1. Disease Induction and Test Compound Administration in a Non-Alcoholic Steatohepatitis Treatment Model The MCD model, which is an animal model of steatohepatitis, was used. C57BL/6 mice were supplied with a MCD (methionine-choline deficient) diet for 5 days, followed by a normal diet for 2 days. In this way, for 10 weeks, the MCD diet and normal diet were alternately supplied. Animals were identified using tail marks during the acclimatization period (blue), dosing and observation period (red). Individual identification cards, distinguished by color, were attached to the breeding box, and an animal room usage record was attached to the entrance of the breeding room.

During the acclimatization period, blood biochemical tests and body weight measurements were performed. Mice were randomly distributed so that the average of each group was distributed as uniformly as possible according to the ranked ALT and body weight levels. [10 animals in the normal feed group (G1), 40 animals in the MCD diet group (G2-G5)]

The improvement effect that appeared when the test compound was repeatedly administered for 6 weeks to the non-alcoholic steatohepatitis C57BL/6 mouse model induced over 10 weeks with the MCD diet was evaluated. Test compound was administered once a day for 6 weeks. As a positive control, obeticholic acid (hereinafter referred to as OCA), which is currently undergoing a phase 3 clinical trial with non-alcoholic steatohepatitis as an indication, was used.

In the case of a control compound (obeticholic acid, 10 mg/kg/day), an appropriate amount was weighed and then diluted in sterile distilled water and administered. In the case of the test compound, after weighing the appropriate amount, it was diluted with 0.5 wt % methyl cellulose aqueous solution to which 1 wt % Tween 80 was added. During oral administration, the weight of the mouse was measured, and the animals were fixed using the cervical skin fixation method, and each test compound was administered using a sonde for oral administration.

Example 2. Observation and Test Items in a Non-Alcoholic Steatohepatitis Treatment Model (1) Weight Measurement It was measured at the start of administration, and once a week and on the day of autopsy after the start of administration.

(2) Feed Intake

It was measured right before the start of administration, and once a week after the start of administration of the test compound. As for the measurement method, the remaining amount of feed was measured per unit of breeding box next day after quantitative feeding, the difference was calculated, and the average intake per mouse was calculated.

(3) Blood Biochemical Test

The following items were tested using a blood biochemical analyzer (7180 Hitachi, Japan) with blood collected and separated at right before and the 6th week (the day of autopsy) after administration of the test compound.

Test items before administration: ALT (alanine transaminase), AST (aspartate transaminase)

Six weeks after administration of the test compound: ALT (alanine transaminase), AST (aspartate transaminase), TG (triglyceride), TCHO (total cholesterol), HDL (high-density lipoprotein), LDL (low-density lipoprotein), GGT (Gamma-glutamyltransferase), LDH (Lactate dehydrogenase)

(4) Autopsy

On the day of autopsy, pimonidazole was diluted in saline at a concentration of 30 mg/ml, and then administered intravenously at a dose of 60 mg/kg. Animals were euthanized 90 minutes after administration. At each autopsy, the animals were inhaled with ether, and when anesthesia was confirmed, blood was collected from the posterior vena cava using a syringe. Thereafter, the abdominal aorta and posterior vena cava were cut, bleeding, and killed. Blood was injected into a vacutainer tube containing a clot activator, allowed to stand at room temperature for about 15 minutes to coagulate, and then centrifuged at 3,000 rpm for 10 minutes to separate the serum. Serum was stored in a deep freezer set at −70° C. or lower before analysis, and was used for blood biochemical tests.

At autopsy, the liver was excised and weighed, the right lobe of the liver was fixed in 10% neutral buffered formalin solution, and the left lobe was divided into half and rapidly frozen using liquid nitrogen. The quick-frozen specimens were stored in a cryogenic freezer set at −70° C. or lower until ELISA analysis.

(5) ELISA Analysis

The contents of TG and TCHO in liver tissue were analyzed using the liver extracted at autopsy. Analysis was carried out using a commercially available ELISA kit.

(6) Histopathological Examination

The fixed tissue was prepared for histopathological examination through general tissue processing processes such as trimming, dehydration, paraffin embedding, and cutting, and then Hematoxylin & Eosin (H&E), Oil-Red-O staining and Masson trichrome staining were performed. And histopathological changes were observed using an optical microscope (Olympus BX53, Japan).

(7) Statistical Analysis

The normality of the data was assumed for the results of this experiment, and analysis was performed using parametric multiple comparison procedures or non-parametric multiple comparison procedures.

If the parametric One-way ANOVA result was significant, a post-hoc comparison test was performed using Dunnett's multiple comparison test, and if the non-parametric Kruskal-Wallis'H-test result was significant, the Dunn's multiple comparison test was used for the post-hoc comparison test.

Statistical analysis was performed using Prism 5.03 (GraphPad Software Inc., San Diego, CA, USA), and a p value of less than 0.05 was determined to be statistically significant.

Example 3. Test Results in a Non-Alcoholic Steatohepatitis Treatment Model (1) Weight Measurement As a result of body weight measurement, the body weight level of all MCD diet groups (G2-G5) during the entire experiment period was significantly lower than that of the normal control group (G1) ($p<0.001$). This is a commonly observed phenomenon when feeding on an MCD diet.

(2) Feed Intake

As a result of measuring feed intake, no significant difference was observed in all test groups compared to the normal control group (G1), the vehicle control group (G2), and the positive control group (G3) during the entire experiment period.

(3) Blood Biochemical Test

As a result of blood biochemical tests, ALT and AST levels of all MCD diet groups (G2-G5) were significantly higher than those of the normal control group (G1) at the start of administration of the test substance (p<0.001), and TG, TCHO, and HDL levels were statistically significantly lower than that of the normal control group (G1) (p<0.001). At 6 weeks after administration of the test compound, the ALT and AST levels of all MCD diet groups (G2-G5) were significantly higher than that of the normal control group (G1) (p<0.001 or p<0.01), and the ALT and AST levels of G5 was significantly lower than that of the vehicle control group (G2) (p<0.001 or p<0.05). At 6 weeks after administration of the test compound, the ALT levels of G3 and G4 were significantly lower than those of the vehicle control group (G2) (p<0.05), and the TG, TCHO, and HDL levels of all MCD diet groups (G2-G5) were significantly lower than those of normal control group (G1) (p<0.001). At 6 weeks after administration of the test compound, the LDL levels of all MCD diet groups (G2-G5) were significantly lower than that of the normal control group (G1) (p<0.001 or p<0.01), and the LDL levels of G4 and G5 were significantly lower than those of the vehicle control group (G2) and the positive control group (G3) (p<0.01). At 6 weeks after administration of the test compound, the LDH level of G3 was significantly higher than that of the normal control group (G1) (p<0.05).

The results are summarized and shown in FIGS. 1 and 2.

FIG. 1 shows the results of blood biochemical analysis after 6 weeks of administration in a non-alcoholic steatohepatitis disease model. Indices of liver function, ALT and AST, showed a statistically significant decrease in dose-dependent manner in the test group, and LDL cholesterol showed a statistically significant decrease compared to G1, G2, and G3.

FIG. 2 is a measurement result of LDH (Lactase Dehydrogenase). It is known that LDH is often increased in ischemic hepatitis, and is associated with liver injury. It can be seen that the test compound of Chemical Formula 1 tends to decrease LDH compared to the positive control group, and in particular, in the high-dose administration group, exhibits a concentration similar to that of the normal group.

(4) Liver Weight Measurement

The resulting values, absolute weight and relative weight, are shown in FIG. 3. As a result of measuring liver weight, the liver weight level of all MCD diet fed groups was significantly lower than that of the normal control group (G1) (p<0.001), and the liver weight level of G5 was significantly lower than that of the vehicle control group (G2) (p<0.05). The relative liver weight level of G2 was significantly higher than that of the normal control group (G1) (p<0.05), and the relative liver weight level of G5 was significantly lower than that of the vehicle control group (G2) and the positive control group (G3) (p<0.01 or p<0.05).

(5) Analysis of Fat in Liver Tissue

The analysis results are shown in FIG. 4. As a result of ELISA analysis, the TG and TCHO levels of all MCD diet groups (G2-G5) were significantly higher than that of the normal control group (G1) (p<0.001), and the TG and TCHO levels of G4 and G5 were significantly lower than that of the vehicle control group (G2) (p<0.001, p<0.01, or p<0.05).

(6) Histopathological Examination

The histopathological examination results are shown in FIG. 5. Microvesicular steatosis and inflammation levels of all MCD diet groups (G2-G5) were significantly higher than those of the normal control group (p<0.01 or p<0.05), and microvesicular steatosis level of G5 was observed to be significantly lower than that of the vehicle control group (p<0.05).

Oil red O and Masson Trichrome staining area levels of all non-alcoholic steatohepatitis-induced groups (G2-G5) were significantly higher than that of the normal control group (p<0.001), and oil red O staining area levels of G4 and G5 were significantly lower than that of the vehicle control group (p<0.01).

Hydroxyproline expression area levels of G2, G3, and G4 were significantly higher than that of the normal control group (G1) (p<0.001 or p<0.05), and the expression area levels of hydroxyproline in G3, G4 and G5 were significantly lower than that of the vehicle control group (G2) (p<0.001 or p<0.01).

Overall, as a result of histopathological examination, the level of microvesicular steatosis in the high-dose group of the test compound was significantly lower than that of the vehicle control group, and the result of measuring the fat area using Oil red O staining and the area of expression of hydroxyproline, an indicator of liver fibrosis, was also observed to be significantly lower than those of the vehicle control group. On the other hand, the test compound administration group showed lower levels of inflammation than the vehicle control group.

(7) Overall Opinion

Under these test conditions, when the test compound was repeatedly administered for 6 weeks to the non-alcoholic steatohepatitis C57BL/6 mouse model induced by the methionine and choline deficient (MCD) diet, ALT, AST and LDL levels, which are values related to liver function, of the test compound group show a statistically significant change in a dose-correlated manner compared to the vehicle control group. Also, the relative weight level of the liver of the test compound group was observed to be significantly lower in a dose dependent manner than that of the vehicle control group. In addition, as a result of histopathological examination, a significant decrease in microvesicular steatosis level, oil red O area level, and hydroxyproline level were observed, and as a result of TG and TCHO analysis in liver tissue, TCHO and TG levels in liver tissue of the test compound group was observed to be significantly lower than those of the vehicle control group. In particular, in the case of the high dose administration group of the test compound, a number of items such as blood biochemistry, liver relative weight, TG and TCHO content in liver tissue, and microvesicular steatosis level were lower than those of the positive control group.

Therefore, it was confirmed that the repeated administration of the test compound under this test condition has the effect of alleviating non-alcoholic steatohepatitis, and the effect of the test compound 30 mg/kg/day was confirmed to be superior to that of the positive control compound.

In particular, considering the fact that OCA, a positive control, showed stomach pain and fatigue in more than 10% of subjects in clinical trials, and in about 10% of subjects, side effects like irregular heartbeat, dry skin, constipation, joint pain, peripheral edema, sore throat, thyroid hormone irregularity, rash, etc. occurred, the usefulness of Compound Formula 1 of the present invention is considered to be very great.

Example 4. Disease Induction and Administration in a Non-Alcoholic Steatohepatitis Prevention Model The efficacy of the test compound for preventing non-alcoholic steatohepatitis was evaluated. Using 7-week-old mice (C57BL/6), the normal group (G1) was supplied with general feed, and the vehicle control group (G2), positive control group (G3), and test groups (G4, G5) were supplied with the MCD feed for 12 weeks. Simultaneously with the MCD diet, test compounds and controls were administered orally once a day. Mice were divided into five groups, and a total of 75 mice, 15 mice per each group, were used for the experiment.

In order to evaluate the prophylactic efficacy, the test compound was administered for 12 weeks at the same time as induction with the MCD diet, and the efficacy of the test compound for the prevention of steatohepatitis was evaluated.

Each appropriate amount of the control compound (Obeticholic acid, 10 mg/kg/day) and the test compound was weighed, and then diluted in 0.5 wt % methyl cellulose aqueous solution to which 1 wt % Tween 80 was added. During oral administration, the weight of the mouse was measured, and the animals were fixed using the cervical skin fixation method, and each test substance was administered using a sonde for oral administration.

Example 5. Test Results in a Non-Alcoholic Steatohepatitis Prevention Model (1) Weight Measurement As a result of body weight measurement, the body weight level of all MCD diet groups (G2-G5) during the entire experiment period was significantly lower than that of the normal control group (G1) ($p<0.001$). This is a commonly observed phenomenon when feeding on an MCD diet.

(2) Feed Intake

As a result of measuring feed intake, no significant difference was observed in all test groups compared to the normal control group (G1), the vehicle control group (G2), and the positive control group (G3) during the entire experiment period.

(3) Analysis of Triglycerides in Liver Tissue

The liver tissues of mice were extracted from the 5 groups, samples were extracted using the Lipid Extraction Kit (Cell biolabs, USA) equipment, and triglycerides in the liver tissues were analyzed using a biochemical analyzer (7020, hitachi, Japan).

Experimental results are expressed using mean and standard deviation, and for comparison between groups, ANOVA analysis is performed using Software StatView (Version 4.51, Abacus Concepts, Berkeley, CA), and if significance is recognized, post-hoc comparison test is performed by Fisher's PLSD. The significance was verified at a significance level of 5% by comparing the groups.

The analysis results after 12 weeks of administration are shown in FIG. 6. As a result of analysis after 12 weeks of administration, a statistically significant decrease in triglycerides was found in the positive control group (G3) and the test group (G4, G5) compared to the vehicle control group (G2). These results indicate that the compound of Chemical Formula 1 dose-dependently inhibits the accumulation of triglycerides in hepatocytes in a disease prevention model for non-alcoholic steatohepatitis.

(4) Overall Opinion

From the above results, it was confirmed that the compound according to the present invention has a prophylactic effect on non-alcoholic steatohepatitis.

The invention claimed is:

1. A method for treating or preventing non-alcoholic steatohepatitis, the method comprising administering to a subject in need thereof a therapeutically or prophylactically effective amount of a pharmaceutical composition comprising a pyrimidine-4-carboxamide compound of Chemical Formula 1 as an active ingredient, wherein Chemical Formula 1 is

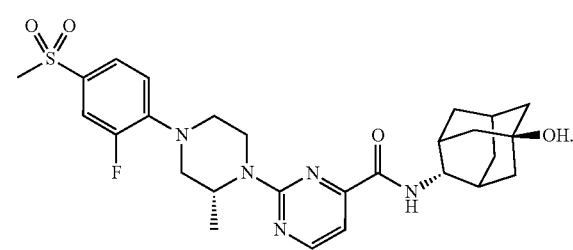 [SMILES: C[C@@H]1CN(c2ccc(S(C)(=O)=O)cc2F)CCN1c1nccc(C(=O)N[C@H]2C3CC4CC2C[C@](O)(C4)C3)n1]

2. The method of claim 1, wherein administering the pharmaceutical composition to the subject alleviates fibrosis symptoms of liver in the subject.

3. A method for treating or preventing liver fibrosis, the method comprising administering to a subject in need thereof a therapeutically or prophylactically effective amount of a pharmaceutical composition comprising a pyrimidine-4-carboxamide compound of Chemical Formula 1 as an active ingredient, wherein Chemical Formula 1 is

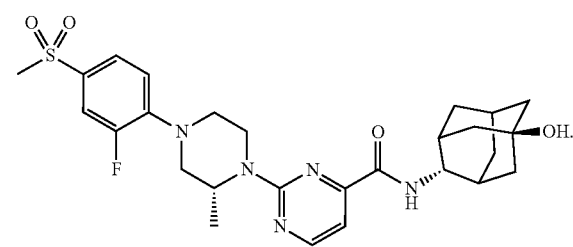 [SMILES: C[C@@H]1CN(c2ccc(S(C)(=O)=O)cc2F)CCN1c1nccc(C(=O)N[C@H]2C3CC4CC2C[C@](O)(C4)C3)n1]

* * * * *